United States Patent
Jin et al.

(10) Patent No.: US 9,028,832 B2
(45) Date of Patent: May 12, 2015

(54) HUMANIZED ANTI-EGFR ANTIBODY L4-H3 AND CODING GENE THEREOF

(75) Inventors: Yanwen Jin, Beijing (CN); David Weaver, Newton, MA (US); Michael Rynkiewicz, Newton, MA (US); Cheng Cao, Beijing (CN)

(73) Assignee: HeFei Tairui Biotechnology Co., Ltd., HeFei, AnHui Province (CN)

( * ) Notice: Subject to any disclaimer, the term of this patent is extended or adjusted under 35 U.S.C. 154(b) by 0 days.

(21) Appl. No.: 13/982,173

(22) PCT Filed: Mar. 25, 2011

(86) PCT No.: PCT/CN2011/000501
§ 371 (c)(1),
(2), (4) Date: Aug. 13, 2013

(87) PCT Pub. No.: WO2012/100384
PCT Pub. Date: Aug. 2, 2012

(65) Prior Publication Data
US 2013/0330362 A1  Dec. 12, 2013

(30) Foreign Application Priority Data

Jan. 27, 2011  (CN) .......................... 2011 1 0029453

(51) Int. Cl.
| C07K 16/00 | (2006.01) |
| A61K 39/395 | (2006.01) |
| C07K 16/30 | (2006.01) |
| C07K 16/28 | (2006.01) |

(52) U.S. Cl.
CPC ............ *C07K 16/30* (2013.01); *C07K 16/2863* (2013.01); *C07K 2317/24* (2013.01); *C07K 2317/92* (2013.01); *C07K 2317/56* (2013.01); *C07K 2317/76* (2013.01)

(58) Field of Classification Search
None
See application file for complete search history.

(56) References Cited

PUBLICATIONS

Paul, Fundamental Immunology, 3rd edition, 1993, pp. 292-295.*
Bendig (1995) Methods: a companion methods in encymology 8: 83-93.*
MacCallum et al. (1996) J. Mol. Biol. 262: 732-745.*
Casset et al. (2003) BBRC 307: 198-205.*
Brochet, Xavier, Marie-Paule Lefranc, and Véronique Giudicelli. "IMGT/V-QUEST: the highly customized and integrated system for IG and TR standardized VJ and VDJ sequence analysis." Nucleic acids research 36.suppl 2 (2008): W503-W508.
Ehrenmann, François, Quentin Kaas, and Marie-Paule Lefranc. "IMGT/3Dstructure-DB and IMGT/DomainGapAlign: a database and a tool for immunoglobulins or antibodies, T-cell receptors, MHC, IgSF and MhcSF." *Nucleic acids research* (2009): gkp946.
"Adalimumab," Drug Bank, Jun. 13, 2005, http://www.drugbank.ca/drugs/DB00051, pp. 1-10.
"Rituximab," Drug Bank, Jun. 13, 2005, http://www.drugbank.ca/drugs/DB00073, pp. 1-9.
"Human (hybridoma H210) anti-hepatitis A IgG variable region, constant region, complementarity-determining regions mRNA, complete cds," NCBI, retrieved on Nov. 3, 2014, http://www.ncbi.nlm.nih.gov/nuccore/M87789.1, pp. 1-2.
Lewis, Alan P., et al. "Rescue, expression, and analysis of a neutralizing human anti-hepatitis A virus monoclonal antibody." The Journal of Immunology 151.5 (1993): 2829-2838.
International Search Report for International Application No. PCT/CN2011/000501, mailed on Nov. 3, 2011.
Sun et al., "Construction and expression of humanized anti-EGFR antibody," *Bull Acad Mil Med Sci*, vol. 33(6), pp. 526-530 (Dec. 2009).

* cited by examiner

*Primary Examiner* — Michael Pak
(74) *Attorney, Agent, or Firm* — Knobbe Martens Olson & Bear LLP

(57) ABSTRACT

A humanized anti-EGFR antibody L4-H3 and gene encoding the antibody are disclosed. The antibody is composed of a heavy chain and a light chain. The amino acid sequence of the heavy chain variable region is shown as positions 1-145 of SEQ ID NO: 3, the heavy chain constant region is the heavy chain constant region of the human antibody IgG1, and the amino acid sequence of the light chain is shown as SEQ ID NO: 1.

4 Claims, 2 Drawing Sheets

HUMANIZED ANTI-EGFR ANTIBODY L4-H3 AND CODING GENE THEREOF

CROSS-REFERENCE TO RELATED APPLICATIONS

This application is the U.S. National Phase under 35 U.S.C. §371 of International Application PCT/CN2011/000501, filed Mar. 25, 2011, which was published in a non-English language, which claims priority to CN 201110029453.3, filed Jan. 27, 2011.

REFERENCE TO SEQUENCE LISTING

This application incorporates by reference the sequence listing submitted as ASCII text filed via EFS-Web on Jul. 26, 2013. The Sequence Listing is provided as a file entitled "SEQ LST US JEEK12-3.txt," created on Jul. 26, 2013, and which is approximately 12 kilobytes in size.

TECHNICAL FIELD

The present invention relates to an anti-EGFR humanized antibody L4-H3, as well as coding gene and applications thereof.

BACKGROUND OF THE INVENTION

The Epidermal Growth Factor Receptor (EGFR) is one member of Epidermal Growth Factor Receptor gene (erbB) family, which is over-expressed in about 30% human tumours, especially in non-small cell lung cancer, head and neck squamous cell carcinoma and colorectal cancer, and the like. Many studies at home and abroad have demonstrated that the antibodies against the EGFR show better therapeutic effect to various human tumours caused by EGFR over-expression or/and mutation, especially head and neck squamous cell carcinoma (80%-100%), colorectal cancer (25%-77%), non-small cell lung cancer (40%-80%), and the like, by means of effectively blocking the binding of the ligands extracellularly to inhibit the EGFR signal transduction pathway. The Epidermal Growth Factor Receptor has become one of tumour treating targets that currently are deeply studied and attract much attention. Using gene engineering to research and prepare the anti-EGFR monoclonal antibody has become one of research hotspots in tumour immune treatment.

In 2004 and 2006, U.S. FDA successfully approved murine-human chimeric antibody cetuximab and whole human antibody panitumumab against EGFR for the treatment of colorectal cancer; and in 2005, anti-EGFR humanized antibody nimotuzumab obtained the first class of new drug certificate approved by the Chinese State Food and Drug Administration (SFDA), and currently, its II/III phase clinical trials are being performed. When used in human body, the murine derived monoclonal antibody may elicit human anti-murine antibody response, thereby to negatively impacting its function. Engineered murine-human chimeric antibody with gene engineering technique may greatly reduce immunogenicity of murine monoclonal antibody, prolong the half life period of antibody in the body, and mediate immune adjustment and ADCC effect with the help of human immunoglobulin Fc fragments, thereby to enhance the biological effect of the antibody. However, the ability to bind antigen of the chimeric antibody is 98.7% lower than that of murine derived antibody. It has been demonstrated by many pre-clinical trials and clinical trials that cetuximab alone and in combination with chemotherapy/radiotherapy show better therapeutic effect. However, a simple CDR graft tends to cause the decrease of binding affinity between an antigen and an antibody. The panitumumab is a fully human antibody prepared with transgenic mouse technologies, and as compared with chimeric antibody and humanized antibody, has almost 100% humanized sequence, which greatly enhances binding affinity between the antibody and a target. However, such antibody shows drawbacks such as murine glycosylation pattern, short half life period and more hypersensitivity, and the like. Nimotuzumab is a humanized antibody obtained by humanized engineering of anti-EGFR murine derived monoclonal antibody. The light chain gene and heavy chain gene of the antibody are linked to different expression vector, respectively, for expression. Since there is a greater difference between the light chain expression and heavy chain expression, it tends to causes very low expression level of complete antibody molecule.

SUMMARY OF THE INVENTION

One purpose of the present invention is to provide an antibody and coding gene thereof.

The antibody provided by the present invention is composed of a heavy chain and a light chain, wherein the heavy chain is formed by binding a heavy chain variable region to a heavy chain constant region; the amino acid sequence of the heavy chain variable region is shown as sites 1-145 of SEQ ID NO:3; the heavy chain constant region is a heavy chain constant region of humanized antibody IgG1; and the amino acid sequence of the light chain is shown as SEQ ID NO:1.

Specifically, the amino acid sequence of the heavy chain of the antibody described above can be shown as SEQ ID NO:3.

A coding gene of the light chain of the antibody described above is shown in I), II) or III) below:

I) nucleotides sequence thereof shown as sites 85-726 in SEQ ID NO:2 or shown as sites 9-729 in SEQ ID NO:2;

II) a DNA molecule hybridizing with the DNA sequence defined in I) under stringent conditions and coding the light chain;

III) a DNA molecule showing greater than 70% identity to the DNA sequence defined in I) and coding the light chain;

A coding gene of the heavy chain of the antibody described above is shown in 1), 2) or 3) below:

1) nucleotides sequence thereof shown as SEQ ID NO:4;

2) a DNA molecule hybridizing with the DNA sequence defined in 1) under stringent conditions and coding the heavy chain; and 3) a DNA molecule showing greater than 70% identity to the DNA sequence defined in 1) and coding the heavy chain.

The recombinant vectors, recombinant strains, recombinant cells or expression cassettes comprising any one of the coding genes described above also fall into the protection scope of the present invention.

The recombinant vectors described above can specifically be recombinant expression vectors prepared by a method comprising the following steps: inserting the coding gene of the light chain between the Nhe I and EcoR I restriction sites of vector pIRES in the direction from Nhe I restriction site to EcoR I restriction site, to obtain a recombinant vector, denoted as an intermediate recombinant vector; inserting the coding gene of the heavy chain between Xba I and Not I restriction sites of the intermediate recombinant vector in the direction from Xba I restriction site to Not I restriction site. The resultant recombinant vector is a target recombinant expression vector.

The recombinant cells described above may specifically be recombinant cells obtained by introducing the recombinant expression vector described above into starting cells.

Wherein, the starting cells are 293T cells.

The method for preparing any one of the antibodies described above also falls into the protection scope of the present invention.

The method for preparing any one of the antibodies described above can comprise the following step: culturing recombinant cells described above, and collecting supernatant to obtain the antibody.

During culturing the recombinant cells, the light chain of antibody and the heavy chain of antibody are expressed, respectively, and the light chain of antibody and the heavy chain of antibody are self-assembled into the antibody.

Another purpose of the present invention is to provide an inhibitor for inhibiting a signal transduction pathway of an Epidermal Growth Factor Receptor.

The active ingredients of the inhibitor for inhibiting a signal transduction pathway of an Epidermal Growth Factor Receptor provided in the present invention are antibody described above, coding gene described above, recombinant vector described above, recombinant strain described above, recombinant cell described above and/or expression cassette described above.

Another purpose of the present invention is to provide an inhibitor for inhibiting tumour cells invasion.

The active ingredients of the inhibitor for inhibiting tumour cells invasion provided in the present invention is an antibody described above, a coding gene described above, a recombinant vector described above, a recombinant strain described above, a recombinant cell described above and/or expression cassette described above.

Another purpose of the present invention is to provide a product for preventing and/or treating tumours.

The active ingredients of the product for preventing and/or treating tumour provided in the present invention are antibody described above, coding gene described above, recombinant vector described above, recombinant strain described above, recombinant cell described above and/or expression cassette described above.

In the inhibitor or product described above, the tumour is colon cancer; and the tumour cells are SW480 cells.

Use of antibody described above, coding gene described above, recombinant vector described above, recombinant strain described above, recombinant cell described above and/or expression cassette described above for preparing an inhibitor for inhibiting a signal transduction pathway of an Epidermal Growth Factor Receptor also falls into the protection scope of the present invention.

Use of antibody described above, coding gene described above, recombinant vector described above, recombinant strain described above, recombinant cell described above and/or expression cassette described above for preparing an inhibitor for inhibiting a tumour cell invasion also falls into the protection scope of the present invention.

Use of antibody described above, coding gene described above, recombinant vector described above, recombinant strain described above, recombinant cell described above and/or expression cassette described above for preparing a product for preventing and/or treating tumours also falls into the protection scope of the present invention.

In uses described above, the tumour is colon cancer; and the tumour cells are SW480 cells.

The last purpose of the present invention is to provide a protein fragment and coding gene thereof.

The amino acid sequence of the protein fragment provided in the present invention is shown as sites 1-145 of SEQ ID NO:3.

The coding gene of the protein fragment provided in the present invention is shown in a), b) or c) below:

a) nucleotides sequence thereof shown as sites 1-435 in SEQ ID NO:4;

b) a DNA molecule hybridizing with the DNA sequence defined in a) under stringent conditions and coding the protein fragment;

c) a DNA molecule having an greater than 70% identity to DNA sequence defined in a) and coding the protein fragment.

PREFERRED EMBODIMENTS

Figure 1:
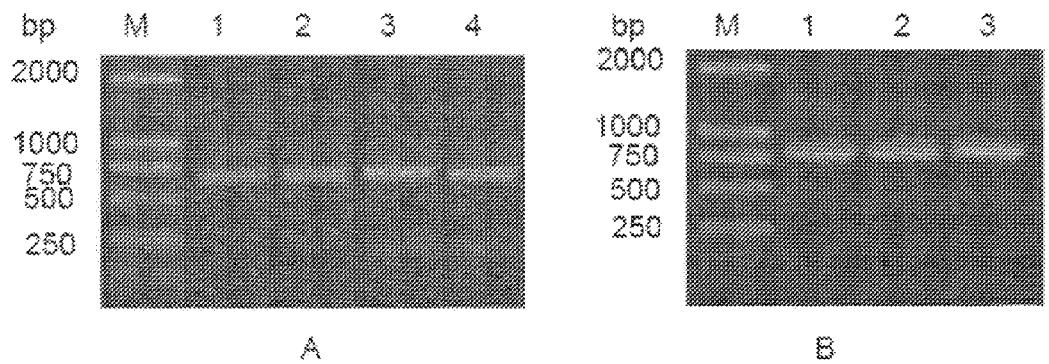
FIG. 1 is an agarose gel electrophoresis plot of the PCR amplified products of the light chain gene and heavy chain variable region gene.

The experimental methods used in the following Examples are all conventional methods, unless otherwise specified.

The materials, agents, and the like used in the following Examples are all commercially available, unless otherwise specified.

pIRES binary expression vector is purchased from Clontech Incorporation, with product catalog number: 631605; and pMD18-T expression vector is purchased from Takara Bio Company, with product catalog number: D504 CA.

The vector, pIRES-Anti-CD20, has been disclosed in "Construction, Expression and Characterization of Anti-CD20 Chimeric Monoclonal Antibody, China Biotechnology 2005, 25(7):34-39", which is publicly available from Institute of Biotechnology, Academy of Military Medical Sciences.

Example 1

The Obtainment of the Coding Genes of the Light Chain and Heavy Chain Variable Region of Antibody The protein structure and the amino acid sequence of the murine-human chimeric antibody, cetuximab, is used as a template for computer modeling design of a new antibody. Following design, the process of synthesis of the genes based on these amino acid sequences of the light chain and the amino acid sequence of "variable region+heavy chain constant region 1" of the heavy chain, is undertaken.

The antibody of the present invention is composed of a light chain L4 and a heavy chain H3; and the heavy chain H3 is composed of a heavy chain variable region (VH), a heavy chain constant region 1 (CH1), a hinge region, a heavy chain constant region 2 (CH2) and a heavy chain constant region 3 (CH3) (H3=VH+CH1+hinge+CH2+CH3). The antibody of the present invention is denoted as L4-H3.

The light chain L4: the amino acid sequence is shown as SEQ ID NO:1; and the coding gene sequence is shown as sites 85-726 in SEQ ID NO:2; The heavy chain H3: the amino acid sequence is shown as SEQ ID NO:3; and the coding gene sequence shown as SEQ ID NO:4;

In SEQ ID NO:3, the amino acids of sites 1-145 are the heavy chain variable region (VH), the amino acids of sites 146-243 are the heavy chain constant region 1 (CH1), the amino acids of sites 244-258 are the hinge region, the amino acids of sites 259-369 are the heavy chain constant region 2 (CH2), and the amino acids of sites 370-475 are the heavy chain constant region 3 (CH3).

In SEQ ID NO:4, the nucleotides of sites 1-435 are the heavy chain variable region (VH) gene, the nucleotides of sites 436-729 are the heavy chain constant region 1 (CH1) gene, the nucleotides of sites 730-739 are a splice donor, the nucleotides of sites 740-1117 are an intron 1, the nucleotides of sites 1118-1162 are hinge region, the nucleotides of sites 1163-1280 are an intron 2, the nucleotides of sites 1281-1613 are heavy chain constant region 2 (CH2), the nucleotides of sites 1614-1710 are an intron 3, the nucleotides of sites 1711-2031 are a heavy chain constant region 3 (CH3), and the nucleotides of sites 2032-2230 are an intron 4.

The "variable region+constant region 1" of the heavy chain H1: the coding gene sequence is shown as SEQ ID NO:5.

The coding gene of the light chain L4 was obtained by artificial synthesis (that is, the nucleotides of sites 9-729 in SEQ ID NO:2 are artificially synthesized). The coding gene of the "constant region 2+constant region 3" of heavy chain H3 (that is, the nucleotides of sites 730-2230 in SEQ ID NO:4) can be obtained by artificially synthesis, and it also can be obtained by enzyme digestion of the vector pIRES-Anti-CD20.

The coding gene of the "variable region+constant region 1" of the heavy chain H3 can be obtained by artificial synthesis, and it also can be obtained according to the following method: artificially synthesizing the coding gene shown as SEQ ID NO:5. The artificially synthesized coding gene shown as SEQ ID NO:5 was used as a template, and the coding gene of "variable region+constant region 1" of the heavy chain H3 was obtained by amplifying from primers 1, 2, 3, 4, 5 and 6 using overlapping PCR method. A fragment (named as A, B, and C) was amplified with the primer pairs 1 and 3, 4 and 5, 6 and 2, respectively. Then, the amplified A, B, and C were mixed as templates, and the target coding gene of "variable region+constant region 1" of the heavy chain H3 was amplified with primers 1 and 2.

chain H1, and lane 3 is the coding gene of the "variable region+constant region 1" of the heavy chain H3.

The obtained coding gene of the light chain and that of the "variable region+constant region 1" of the heavy chain H3 were cloned into vector pMD18-T, respectively, transforming *Escherichia coli* DH5a, picking monoclonal strain, extracting plasmid and sequencing for identification. The results demonstrated that the DNA shown as nucleotides at sites 9-729 in SEQ ID NO:2 (that is, the coding gene of the light chain) had been inserted into vector pMD18-T, and the recombinant vector was denoted as pMD18-T/L4. The nucleotides shown at sites of 1-729 in SEQ ID NO:4 (that is, the coding gene of the "variable region+constant region 1" of the heavy chain H3) had been inserted into vector pMD18-T, and the recombinant vector was denoted as pMD18-T/VH+CH1.

Example 2

The Expression and Purification of the Antibodies

A. Construction of the Recombinant Expression Vector:

The recombinant vector pMD 18-T/L4 and pIRES binary expression vector were enzymatically digested with corresponding restriction endonuclease (NheI and EcoRI), respectively. After agarose gel electrophoresis, the purified target fragments were recovered. The light chain gene fragment L4 and vector fragment were mixed, and reacted with each other for 12 h at 16° C., under the action of linking agents. Transforming *Escherichia coli* DH5a, picking monoclonal strain, extracting plasmid and sequencing for identification. Results: the light chain coding gene shown as nucleotides at sites 9-729 in SEQ ID NO:2 had been inserted between NheI and EcoRI restriction sites of vector pIRES (in the direction from NheI restriction site to EcoRI restriction site). It is demonstrated that the constructed recombinant vector is right, denoted as recombinant expression vector pIRES/L4.

The plasmid large fragment was recovered by using the pIRES/L4 as a template and enzymatic digestion with XbaI and Not I, denoted as fragment 1. A fragment with about 729 bp (that is, the fragment of "variable region+constant region 1" of the heavy chain H3) was recovered by using the pMD18-T/VH+CH1 as a template and enzymatic digestion

```
                                                                  (SEQ ID NO: 6)
1:  5'-gtgtctagagccgccaccatggactgga-3'(XbaI);

(SEQ ID NO: 7)
2:  5'-gggatccacttacctgttgctttct-3'(BamHI);

(SEQ ID NO: 8)
3:  5'-atccactcaagtctttgtccaggggcctgtcgcacccagtggacgccgtagttagtcaggctgaatccag-3';

(SEQ ID NO: 9)
4:  5'-gagtggatgggagtgatctggagtggtggtaacactgactacaacaccccttcactagcagagtcacc-3'.

(SEQ ID NO: 10)
5:  5'-gaccagggttccctggccccagtaggcgaactcgtagtcgtaataagtcagggctctcgcacag-3'

(SEQ ID NO: 11)
6:  5'-cctactggggccagggaaccctggtcaccgtctcctcagcctccaccaagggcccatcg-3'.
```

Figure 2:
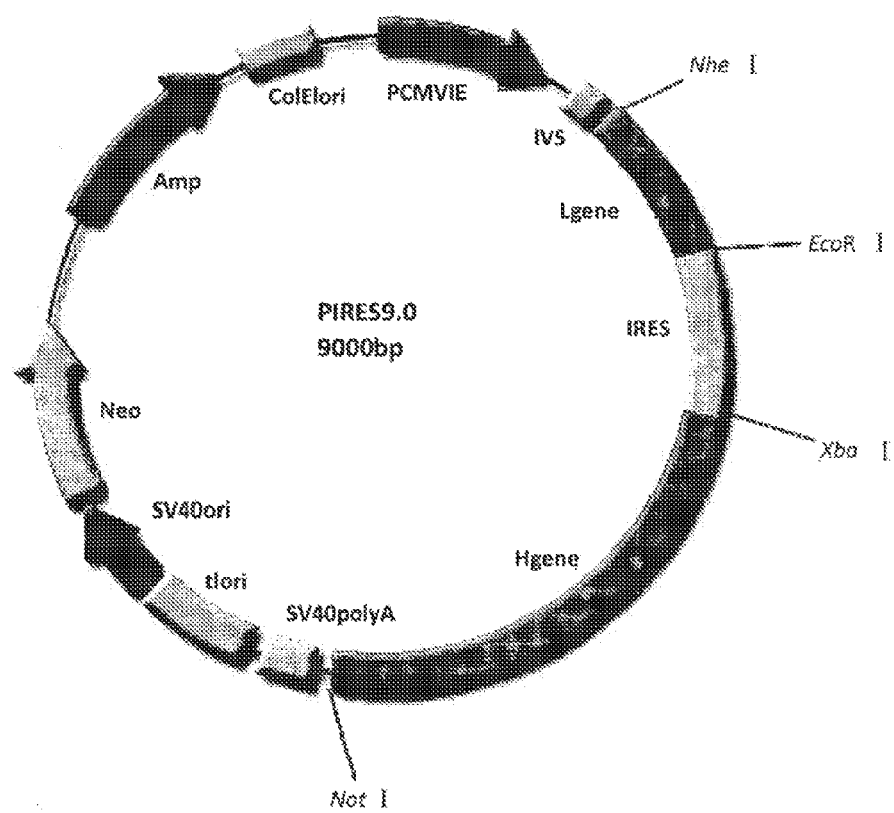
FIG. 2 is a schematic illustration of the expression vector comprising the antibody of the present invention.

The gel electrophoresis assay was performed on the respective genes obtained, and the results are consistent with the expected size. The fragment size of the light chain L4 is about 720 bp, and the size of the coding gene of the "variable region+constant region 1" of the heavy chain H3 is about 729 bp (FIG. 1). M. relative molecular mass standard; A: lane 1 is the coding gene of the light chain L4; B: lane 1 is the coding gene of the "variable region+constant region 1" of the heavy with Xba I and BamH I, denoted as fragment 2. A fragment with about 1502 bp (that is, a fragment comprising "constant region 2+ constant region 3 of the heavy chain") was recovered by using the pIRES-Anti-CD20 as a template and enzymatic digestion with BamH I and Not I, denoted as fragment 3. The fragments 1, 2 and fragment 3 are linked to obtain a recombinant vector, transforming *Escherichia coli* DH5a, picking monoclonal strain, extracting plasmid and sequencing for identification. The results demonstrated that the heavy chain coding gene shown as SEQ ID NO:4 had been inserted between the XbaI and Not I restriction sites of vector pIRES (in the direction from Xba I to Not I); the light chain coding gene shown as nucleotides at sites 9-729 in SEQ ID NO:2 had been inserted between the EcoRI and NheI restriction sites of vector pIRES (in the direction from Nhe I to EcoR I); and IRES (Internal ribosome entry site, IRES may independently recruit ribosomes to translate the heavy chain mRNA) was located between the light chain coding gene and heavy chain coding gene. The positive recombinant expression vector was denoted as pIRES/L4/H3 (FIG. 2).

B. The Vector Transformation and the Expression of the Antibodies 293T cells (293T human embryonic kidney T cells) were purchased from American Type Culture Collection (ATCC) with product catalog number CRL-11268; Lipofectamine 2000 was purchased from Invitrogen Corporation with product catalog number 12566014; HyQSFM4CHO medium was purchased from HyClone Incorporation with product catalog number SH30518.02; and rProtein A chromatographic column was purchased from GE Incorporation with product catalog number 17-5079-01.

The 293T cells were inoculated in culture dishes with 10 cm diameter at the density of $1 \times 10^6$/ml, respectively. The culture dishes were filled with DMEM medium containing 10% fetal bovine serum, and were cultured in 5% $CO_2$ incubator at 37° C. 5 μg of plasmid pIRES/L4/H3 obtained in step A was used to transfect 293T cells, with the detail operation according to the description of the agent Lipofectamine 2000. The recombinant cells 293T-pIRES/L4/H3 were obtained.

The recombinant cells 293T-pIRES/L4/H3 were cultured with serum free DMEM medium. After 6-8 h, the serum free medium was drawn off, and was replaced with HyQSFM4CHO medium. The culture last totally for 84 h under the same conditions, and the cell supernatant was collected once every 12 h. Then the expression of the antibody was roughly assessed using ELISA method. The transfection system was amplified, and cell culture supernatant of 4-5 L was collected, which was adjusted to pH 6.0-7.0, and was filtered via 0.45 μm filter membrane, and the antibody was then purified with a rProtein A chromatographic column, with the detail operation according to the product description.

ELISA: Double Antibody Sandwich Method for Assaying Unknown Antigen:

1. Coating: 0.05M PH9.0 carbonate coating buffer was used to dilute the antibody (primary antibody is goat anti-human IgG), until the content of protein is 1~10 μg/ml. In each reaction well of the polystyrenes plate, 0.1 ml is added, overnight at 4° C. On the following day, the solution inside the well was discarded, and the plate was washed with washing buffer thrice, 3 minutes for each. (Simplified as washing, the same below).

2. Loading: the coated reaction wells were loaded with 0.1 ml of the sample to be tested and diluted in certain proportions, and was incubated at 37° C. for 1 hour, and washed. Alternatively, a blank well, a negative control well (the 293T cell supernatant of untransfected plasmid) and positive control well (cetuximab injection (Erbitux), Imported Drug License Number: S20050095. MERCK & CO. INC., Germany, Product Lot Number: 7667201) were loaded.

3. Addition of enzyme-labeled antibody (secondary antibody is goat anti-human IgG-HRP (goat anti-human IgG-horseradish peroxidase)): 0.1 ml of freshly diluted enzyme-labeled antibody (the dilution after titration) was added into each reaction well, which was incubated at 37° C. for 0.5-1 hour, and washed.

4. Addition of substrate solution for color development: 0.1 ml of temporarily formulated TMB substrate solution was added into each reaction well, at 37° C. for 10-30 minutes.

5. Quenching the reaction: 0.05 ml of 2M sulfuric acid was added into each reaction well.

6. Assessing the results: the results may be observed by the naked eye directly on the white background, where the deeper the color inside the reaction well indicated a stronger positivity; and the negative reaction was colorless or very light. "+", "−" indicators were used according to the degree of the color. The OD value can be measured: after zero adjustment with blank control well, the OD value of each well was measured on ELISA instrument, at 450 nm (if colored with ABTS, at 410 nm). If the OD value was greater than that of predetermined negative control by a factor of 2.1, it was positive.

Agents (1) The coating buffer (PH9.6, 0.05M of carbonate buffer): $Na_2CO_3$ 1.59 g, $NaHCO_3$ 2.93 g, adding distilled water to 1000 ml.

(2) The washing buffer (PH7.4, PBS): 0.15M: $KH_2PO_4$ 0.2 g, $Na_2HPO_4.12H_2O$ 2.9 g, NaCl 8.0 g, KCl 0.2 g, Tween-20 0.05% 0.5 ml, adding distilled water to 1000 ml.

(3) The dilution: 0.1 g of Bovine Serum Albumin (BSA) was added into the washing buffer, totally 100 ml, or goat serum, rabbit serum, and the like was prepared into 5-10% as along with the washing solution for use.

(4) The quenching solution (2M $H_2SO_4$): 178.3 ml of distilled water was added into 21.7 ml of the concentrated sulfuric acid (98%) dropwise.

Sodium phosphate buffer (binding buffer): as the binding buffer for purifying Protein A. Method for formulation: 57.7 ml of 1M $Na_2HPO_4$ and 42.3 ml of 1M $NaH_2PO_4$ were mixed uniformly to obtain 100 ml of 0.1M sodium phosphate buffer, pH7.0, which was then diluted with distilled water to 20 mM ready-for-use.

The citric acid-sodium citric acid buffer (extracting buffer): as the extracting buffer for purifying Protein A. The method for formulation: 186 ml of 0.1M citric acid and 14 ml of 0.1M sodium citric acid were mixed uniformly to obtain 200 ml of 0.1M citrate buffer, pH3.0.

The antibody was purified with rProtein A chromatographic column: the purification medium: HiTrap rProtein A FF, 5 ml, was purchased from GE Incorporation, Lot Number: 17-5079-01. For the detailed usage description, please refer the description provided by this company.

Procedures:

1) Washing the tubing with 1M NaOH and $ddH_2O$ in this order, boiling the small filter in 0.1M NaOH for 10 min, and then immersing it into $ddH_2O$ for 1-2 min;

2) Setting the program to connect the rProtein A affinity chromatography column;

3) Equilibrating chromatography column with 20 mM binding buffer (pH7.0);

4) Loading the prepared cell supernatant at the flow rate of 1-2 ml/min; preparing the cell supernatant: taking out supernatant after centrifugating at 12000 g for 15 min, then passing the supernatant through 0.22 um cellulose nitrate filter membrane for filtration sterilization.

5) Extracting the target proteins with 1M extracting buffer (pH3.0) just before the end of the loading;

6) Collecting the extracting solution (that is, the target proteins), adjusting the pH to 7.0 with Trise base (pH9.0), and then assaying by electrophoresis; and 7) Washing the tubing and small filter according to step 1).

C. The Protein Assay

The goat anti-human IgG-HRP antibody was purchased from Sigma Corporation with product catalog number (046K4801); and goat anti-murine IgG1 was purchased from SBA (Southern Biotechnology Associates, Inc.) with product catalog number (1010-05);

SDS-PAGE: 15 µl extracting solution (that is, the antibody solution) was taken out to perform the reduced SDS-PAGE electrophoresis on 12% gel, staining with Coomassie brilliant blue R-250.

Figure 3:
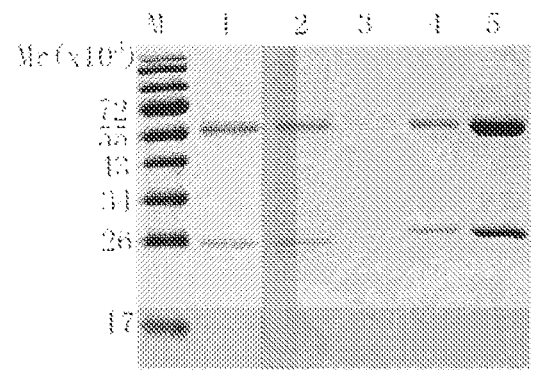
FIG. 3 is a reduced SDS-PAGE assay of the antibody of the present invention.

The results show that the relative molecular weights of the heavy chain and light chain of antibody obtained via purification are $25 \times 10^3$, $50 \times 10^3$, respectively (FIG. 3), consistent with the expected results. In FIG. 3, lanes 1-4 represent the antibody L4-H3 of the present invention; and lane 5 represents positive control cetuximab.

Figure 4:
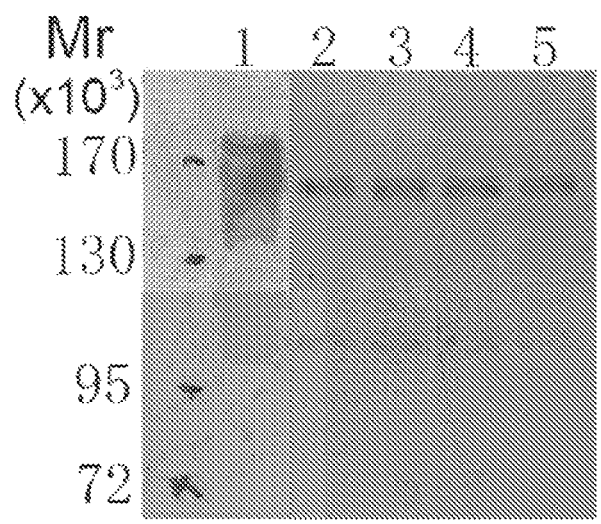
FIG. 4 is an immunoblotting assay of the antibody of the present invention.

Immunoblotting assay: another portions of extracting solution was taken out to perform reduced SDS-PAGE electrophoresis on 12% gel, and then was transferred to cellulose nitrate membrane. Then the membrane was taken out and blocked in blocking buffer (1×PBST containing 5% defatted milk powder) at room temperature for 2 h, was incubated with the 1:5000 diluted goat anti-human IgG-HRP antibody for 2 h (at room temperature), and then was washed with 1×PBST thrice. Finally, the membrane was colored with ECL, and was exposed to x-ray film. In FIG. 4, lane 1 represents the positive control cetuximab; and lanes 2-5 represent the antibody L4-H3 of the present invention.

Immunoblotting (12%) assay demonstrates that the antibody can specifically be bound to the goat anti-human IgG However, there are partial non-specific hybridized lanes that react with anti-human IgG secondary antibody (including the commercialized cetuximab), which may be derived from the mixing of partial non-whole length heavy chain fragments during the purification. However, above results do not influence the assessment to antibody binding affinity. None of antibodies described above reacts with goat anti-murine IgG1.

Since the light chain and heavy chain of the present antibody are expressed proportionally in the same expression vector, they are self-assembled into the complete antibody containing two light chains and two heavy chains.

D. Expression Amount of Protein 4-5 L of cell culture supernatant of expression antibody L4-H3 was obtained according to the method in steps A and B. The antibody was purified by rProtein A chromatography column to assay the expression amount of the antibody in 293T cells, and the result is 0.6 µg/ml extracting solution.

Example 3

The Functional Properties of the Antibody

A. Assay of the Binding Ability of Antibody and Antigen with Surface Plasmon Resonance [Biacore]

Sensor Chip CM5 was purchased from BD Incorporation with product catalog number Br-1000-14; BD BioCoat™ and Matrigel™ Invasion Chamber were purchased from BD Incorporation with product catalog number 354480.

EGFR proteins were purchased from Sigma Corporation with product catalog number E2645-500UN.

The binding affinity between antibody and EGFR was assayed with Biacore3000 equipment. The EGFR proteins diluted with 10 mmol/L NaAc and having different pH (4.0, 4.5, 5.0 and 5.5) were formulated, and were pre-concentrated on CM5 chip to select the NaAc diluted protein with optimum pH. The purified antibody (that is, the washing solution obtained in step B of Example 2) was covalently bound to CM5 sensor chip. The mobile phase was HBS-EP (pH7.4), and flow rate was 20 µl/min. The binding affinities between 5 different concentrations of antibodies (0, 10.55, 21.1, 42.2 and 84.4 nmol/L) and EGFR protein were assayed. The binding affinities were computed with the software attached by Biacore3000. At the same time, the cetuximab was used as a control.

The experiment repeated thrice, and the results were averaged.

The results show that there are good binding activities between the antibody and antigen EGFR, and the binding affinity is $2.75 \times 10^{-9}$ M. the binding affinity of cetuximab is $1.1 \times 10^{-9}$ M. The results demonstrate that the humanized antibody of the present invention maintains the good binding activity of the parental antibody, overcoming the adverse response of murine derived antibody, and possesses the well clinical application value.

B. The Experiment of Tumour Cell Invasion

SW480 cells were purchased from American Type Culture Collection, (ATCC), with ATCC® Number: CCL228™; and cetuximab antibody was purchased from Merck-Lipha Pharmaceuticals Ltd, Germany (the trade name: ERBITUX; the drug name: Cetuximab; the reference trade name in China: ai bi tuo; the molecule structure name: cetuximab; Origin: Germany; Manufacturer: Merck-Lipha Pharmaceuticals Ltd, Germany).

The RPMI1640 medium (purchased from Invitrogen Corporation with catalog number 31800-022) was used to culture SW480 cells. The invasion chamber was hydrated with serum-free RPMI1640 medium, and was incubated for 2 h (37° C., 5% $CO_2$). The serum-free RPMI1640 was discarded, 750 µl of RPMI1640 (containing 10% serum) was added into well chambers of invasion Chamber (BD BioCoat™ Matrigel™ Invasion Chamber, purchased from BD Incorporation with product catalog number 354480); 475 µl of RPMI1640 (containing 1% serum) was added into insert chambers, and then 25 µl digested SW480 cells were added (the numbers of cell $>10^5/500$ µl). Finally, the negative control PBS and the antibody of the present invention were separately added into the insert chambers, and each sample had two repeat wells, with the final concentration of antibody 100 ng/ml. After 24 h incubation, the cells that did not penetrate through the basement membrane of invasion cassette were wiped off with sterilized cotton swabs; and the cells that penetrate through the basement membrane of invasion cassette were fixed, stained, dried at room temperature, and then counted under the light microscope.

Statistics: the number of the corresponding 3 sets of cells of the sample in each insert chamber was counted under 100× microscope. The t-test was performed on the cell invasion experiment data by SPSS12.0 analytic software, and the antibody of the present invention was compared with human IgG set. If the result was P<0.05, the difference between two treatment effects was statistically significant.

The anti-EGFR antibody of the invention has significant difference, and its inhibition to the invasion of SW480 tumour cell is significant. The experiment was repeated thrice, and the results were averaged. The t-test results show that the P values of the sets of human IgG and the antibody of the present invention are less than 0.01 (Table 1), and as compared with human IgG in a control set,

TABLE 1

The result of the t-test result of the cell invasion experiment

| Sets | n (number) | average number of cell |
|---|---|---|
| human IgG | 8 | 146 ± 16.531 |
| antibody of the present invention | 8 | 67 ± 15.334* |

Note:
as compared with human IgG,
*P < 0.01;

INDUSTRY UTILITY

The experimental results demonstrate that the antibody of the present invention has better antigen binding activities and ability to inhibit tumour cell growth, immigration and invasion. In contrast, the binding affinity of the common anti-EGFR human-murine chimeric antibody cetuximab in international market is $1.1 \times 10^{-9}$ M. The humanized antibody of the present invention can bind to the EGFR better, accordingly to insure the anti-tumour effect thereof. The method for preparing the antibody of the present invention can express the light chain and heavy chain simultaneously, causing the expression proportion of the light chain and heavy chain near 1:1, accordingly to produce more rates of matched double-chain antibody. In conclusion, the antibody of the present invention and the preparing method thereof would have wide utility prospect in the field of preventing and/or treating tumours.

What is claimed is:

1. An antibody comprising a heavy chain and a light chain, wherein the heavy chain comprises a heavy chain variable region and a heavy chain constant region, and wherein the amino acid sequence of the heavy chain variable region is set forth at positions 1-145 of SEQ ID NO:3, and wherein the heavy chain constant region is a heavy chain constant region of human antibody IgG1, and wherein the amino acid sequence of the light chain is set forth by SEQ ID NO:1.

2. The antibody according to claim 1, wherein in that the amino acid sequence of the heavy chain of the antibody is set forth by SEQ ID NO:3.

3. An inhibitor for inhibiting a signal transduction pathway of an Epidermal Growth Factor Receptor, an inhibitor for inhibiting tumour cells invasion or a product for preventing and/or treating tumours, comprising the antibody of claim 1 as an active ingredient, wherein the tumour is colon cancer; and preferably the tumour cells are SW480 cells.

4. A protein, comprising the amino acid sequence of the protein fragment which is encoded by a nucleotide sequence as set forth by SEQ ID NO:35 and an amino acid sequence as set forth by SEQ ID NO:1.

* * * * *

UNITED STATES PATENT AND TRADEMARK OFFICE
CERTIFICATE OF CORRECTION

PATENT NO. : 9,028,832 B2  
APPLICATION NO. : 13/982173  
DATED : May 12, 2015  
INVENTOR(S) : Yanwen Jin et al.

Page 1 of 1

It is certified that error appears in the above-identified patent and that said Letters Patent is hereby corrected as shown below:

Title page,

In column 2 (page 1, item 56) at line 4, Under Publications, change "encymology" to --enzymology--.

In the specification,

In column 8 at line 57, Change "um" to --μm--.

In column 8 at line 62, Change "Trise" to --Tris--.

In the claims,

In column 22 at line 19, In Claim 4, Change "SEQ ID NO:35" to --SEQ ID NO:5--.

Signed and Sealed this  
Third Day of May, 2016

Michelle K. Lee  
*Director of the United States Patent and Trademark Office*

SEQUENCE LISTING

```
<160> NUMBER OF SEQ ID NOS: 11

<210> SEQ ID NO 1
<211> LENGTH: 214
<212> TYPE: PRT
<213> ORGANISM: Artificial Sequence
<220> FEATURE:
<223> OTHER INFORMATION: Synthesized

<400> SEQUENCE: 1

Glu Leu Val Met Thr Gln Ser Pro Ser Ser Leu Ser Ala Ser Val Gly
1               5                   10                  15

Asp Arg Val Asn Ile Ala Cys Arg Ala Ser Gln Ser Ile Gly Thr Asn
            20                  25                  30

Ile His Trp Tyr Gln Gln Lys Pro Gly Lys Ala Pro Arg Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Asn Asn Asn Trp Pro Thr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 735
<212> TYPE: DNA
<213> ORGANISM: Artificial Sequence
<220> FEATURE:
<223> OTHER INFORMATION: Synthesized

<400> SEQUENCE: 2
gtggctagcg ccgccaccat ggacatgagg gtccccgctc agctcctggg gctcctgctg      60
ctctggctcc caggtgccag atgtgaactc gtcatgaccc agtctccatc ctccctgtct     120
```

```
gcatctgtag gagacagagt caacattgcc tgccgggcaa gtcagagcat tggcactaac    180
atccactggt atcagcagaa accagggaaa gcccctagac tcctgatcaa atatgcctcc    240
gaaagcatca gtgggtccc atcaagattc agcggcagtg atctggcac agatttcact      300 ctcaccatca gcagcctgca gcctgaagat tttgcaatct attactgtca gcaaaataac    360
aattggccta ctacgttcgg cggagggacc aaggtggaaa tcaaacgaac tgtggctgca    420
ccatctgtct tcatcttccc gccatctgat gagcagttga aatctggaac tgcctctgtt    480
gtgtgcctgc tgaataactt ctatcccaga gaggccaaag tacagtggaa ggtggataac    540
gccctccaat cgggtaactc ccaggagagt gtcacagagc aggacagcaa ggacagcacc    600
tacagcctca gcagcaccct gacgctgagc aaagcagact acgagaaaca caaagtctac    660
gcctgcgaag tcacccatca gggcctgagc tcgcccgtca caaagagctt caacagggga    720
gagtgttagg aattc                                                     735
```

```
<210> SEQ ID NO 3
<211> LENGTH: 475
<212> TYPE: PRT
<213> ORGANISM: Artificial Sequence
<220> FEATURE:
<223> OTHER INFORMATION: Synthesized

<400> SEQUENCE: 3
```

```
Val Ser Arg Ala Ala Thr Met Asp Trp Thr Trp Arg Val Phe Cys Leu
1               5                   10                  15

Leu Ala Val Ala Pro Gly Ala His Ser Gln Val Lys Leu Leu Glu Gln
            20                  25                  30

Ser Gly Ala Glu Val Lys Lys Pro Gly Ala Ser Val Lys Val Ser Cys
        35                  40                  45

Lys Ala Ser Gly Phe Ser Leu Thr Asn Tyr Gly Val His Trp Val Arg
    50                  55                  60

Gln Ala Pro Gly Gln Arg Leu Glu Trp Met Gly Val Ile Trp Ser Gly
65                  70                  75                  80

Gly Asn Thr Asp Tyr Asn Thr Pro Phe Thr Ser Arg Val Thr Ile Thr
                85                  90                  95

Arg Asp Thr Ser Ala Thr Thr Ala Tyr Met Gly Leu Ser Ser Leu Arg
            100                 105                 110

Pro Glu Asp Thr Ala Val Tyr Tyr Cys Ala Arg Ala Leu Thr Tyr Tyr
        115                 120                 125

Asp Tyr Glu Phe Ala Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Ala Glu Pro Lys Ser Cys Asp Lys Thr His Thr Cys Pro Pro
```

```
                     245                 250                 255
Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 4
<211> LENGTH: 2230
<212> TYPE: DNA
<213> ORGANISM: Artificial Sequence
<220> FEATURE:
<223> OTHER INFORMATION: Synthesized

<400> SEQUENCE: 4
gtgtctagag ccgccaccat ggactggacc tggagggtct tctgcttgct ggctgtagct      60
ccaggtgctc actcccaggt gaagctgctg agcagtctg gggctgaagt gaagaagcct     120
ggggcctcag tgaaggtttc ctgcaaggca tctggattca gcctgactaa ctacggcgtc     180
cactgggtgc gacaggcccc tggacaaaga cttgagtgga tggagtgat ctggagtggt     240 ggtaacactg actacaacac ccccttcact agcagagtca ccatcaccag gacacgtcc     300 gctactacag cctacatggg cctgtctagc ctgagacccg aggacacggc cgtatattac     360
tgtgcgagag ccctgactta ttacgactac gagttcgcct actggggcca gggaaccctg     420
gtcaccgtct cctcagcctc caccaagggc ccatcggtct tccccctggc accctcctcc     480
aagagcacct ctggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgacagtgcc ctccagcagc     660
ttgggcaccc agacctacat ctgcaacgtg aatcacaagc ccagcaacac caaggtggac     720
aagaaagcaa caggtaagtg gatccggagg gagggtgtct gctggaagca ggctcagcgc     780
```

| | |
|---|---|
| tcctgcctgg acgcatcccg gctatgcagc cccagtccag ggcagcaagg caggccccgt | 840 |
| ctgcctcttc acccggaggc ctctgcccgc cccactcatg ctcagggaga gggtcttctg | 900 |
| gcttttccc caggctctgg gcaggcacag gctaggtgcc cctaacccag gccctgcaca | 960 |
| caaaggggca ggtgctgggc tcagacctgc caagagccat atccgggagg accctgcccc | 1020 |
| tgacctaagc ccaccccaaa ggccaaactc tccactccct cagctcggac accttctctc | 1080 |
| ctcccagatt ccagtaactc ccaatcttct ctctgcagag cccaaatctt gtgacaaaac | 1140 |
| tcacacatgc ccaccgtgcc caggtaagcc agcccaggcc tcgccctcca gctcaaggcg | 1200 |
| ggacaggtgc cctagagtag cctgcatcca gggacaggcc ccagccgggt gctgacacgt | 1260 |
| ccacctccat ctcttcctca gcacctgaac tcctgggggg accgtcagtc ttcctcttcc | 1320 |
| ccccaaaacc caaggacacc ctcatgatct cccggacccc tgaggtcaca tgcgtggtgg | 1380 |
| tggacgtgag ccacgaagac cctgaggtca agttcaactg gtacgtggac ggcgtggagg | 1440 |
| tgcataatgc caagacaaag ccgcgggagg agcagtacaa cagcacgtac cgtgtggtca | 1500 |
| gcgtcctcac cgtcctgcac caggactggc tgaatggcaa ggagtacaag tgcaaggtct | 1560 |
| ccaacaaagc cctcccagcc cccatcgaga aaaccatctc caaagccaaa ggtgggaccc | 1620 |
| gtggggtgcg agggccacat ggacagaggc cggctcggcc caccctctgc cctgggagtg | 1680 |
| accgctgtac caacctctgt ccctacaggg cagccccgag aaccacaggt gtacaccctg | 1740 |
| cccccatccc gggatgagct gaccaagaac caggtcagcc tgacctgcct ggtcaaaggc | 1800 |
| ttctatccca gcgacatcgc cgtggagtgg gagagcaatg ggcagccgga gaacaactac | 1860 |
| aaggccacgc ctcccgtgct ggactccgac ggctccttct cctctacag caagctcacc | 1920 |
| gtggacaaga gcaggtggca gcaggggaac gtcttctcat gctccgtgat gcatgaggct | 1980 |
| ctgcacaacc actacacgca gaagagcctc tccctgtctc cgggtaaatg agtgcgacgg | 2040 |
| ccggcaagcc cccgctcccc gggctctcgc ggtcgcacga ggatgcttgg cacgtacccc | 2100 |
| gtgtacatac ttcccgggcg cccagcatgg aaataaagca cccagcgctg ccctgggccc | 2160 |
| ctgcgagact gtgatggttc tttccacggg tcaggccgag tctgaggcct gagtggcatg | 2220 |
| agggaggcag | 2230 |

<210> SEQ ID NO 5
<211> LENGTH: 770
<212> TYPE: DNA
<213> ORGANISM: Artificial Sequence
<220> FEATURE:
<223> OTHER INFORMATION: Synthesized

<400> SEQUENCE: 5

| | |
|---|---|
| gtgtctagag ccgccaccat ggactggacc tggagggtct tctgcttgct ggctgtagct | 60 |
| ccaggtgctc actcccaggt gaagctgctg gagcagtctg ggctgaagt gaagaagcct | 120 |
| ggggcctcag tgaaggtttc ctgcaaggca tctggattca gcatcggcaa ctacggcatc | 180 |
| cactgggtgc gacaggcccc tggacaaaga cttgagtgga tgggaggaat ctggagtggt | 240 |
| ggtaacgccg actacgcaca gaaattccag ggcagagtca ccatcaccag ggacacgtcc | 300 |
| gctactacag cctacatggg cctgtctagc ctgagacccg aggacacggc cgtatattac | 360 |
| tgtgcgagag tgggcactta ttacgactac gagttcgacg tgtggggcca gggaaccctg | 420 |
| gtcaccgtct cctcagcctc caccaagggc ccatcggtct tccccctggc acctcctcc | 480 |
| aagagcacct ctgggggcac agcggccctg ggctgcctgg tcaaggacta cttccccgaa | 540 |

```
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actacaggta agtggatccc                770
```

<210> SEQ ID NO 6
<211> LENGTH: 28
<212> TYPE: DNA
<213> ORGANISM: Artificial Sequence
<220> FEATURE:
<223> OTHER INFORMATION: Synthesized

<400> SEQUENCE: 6

```
gtgtctagag ccgccaccat ggactgga                                        28
```

<210> SEQ ID NO 7
<211> LENGTH: 25
<212> TYPE: DNA
<213> ORGANISM: Artificial Sequence
<220> FEATURE:
<223> OTHER INFORMATION: Synthesized

<400> SEQUENCE: 7

```
gggatccact tacctgttgc tttct                                           25
```

<210> SEQ ID NO 8
<211> LENGTH: 70
<212> TYPE: DNA
<213> ORGANISM: Artificial Sequence
<220> FEATURE:
<223> OTHER INFORMATION: Synthesized

<400> SEQUENCE: 8

```
atccactcaa gtctttgtcc aggggcctgt cgcacccagt ggacgccgta gttagtcagg    60
ctgaatccag                                                            70
```

<210> SEQ ID NO 9
<211> LENGTH: 69
<212> TYPE: DNA
<213> ORGANISM: Artificial Sequence
<220> FEATURE:
<223> OTHER INFORMATION: Synthesized

<400> SEQUENCE: 9

```
gagtggatgg gagtgatctg gagtggtggt aacactgact acaacacccc cttcactagc    60
agagtcacc                                                             69
```

<210> SEQ ID NO 10
<211> LENGTH: 64
<212> TYPE: DNA
<213> ORGANISM: Artificial Sequence
<220> FEATURE:
<223> OTHER INFORMATION: Synthesized

<400> SEQUENCE: 10

```
gaccagggtt ccctggcccc agtaggcgaa ctcgtagtcg taataagtca gggctctcgc    60
acag                                                                  64
```

<210> SEQ ID NO 11
<211> LENGTH: 59
<212> TYPE: DNA
<213> ORGANISM: Artificial Sequence

```
<220> FEATURE:
<223> OTHER INFORMATION: Synthesized

<400> SEQUENCE: 11
cctactgggg ccagggaacc ctggtcaccg tctcctcagc ctccaccaag ggcccatcg      59
```